(12) United States Patent
Drader et al.

(10) Patent No.: US 9,097,711 B2
(45) Date of Patent: *Aug. 4, 2015

(54) MULTIPLE-ANALYTE ASSAY DEVICE AND SYSTEM

(71) Applicants: Ibis Biosciences, Inc., Carlsbad, CA (US); Nina M. Hofstadler, Vista, CA (US)

(72) Inventors: Jared J. Drader, San Marcos, CA (US); Gordon Bruce Collier, Fitzroy Harbour (CA); Steven A. Hofstadler, Vista, CA (US)

(73) Assignee: IBIS BIOSCIENCES, INC., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/102,206

(22) Filed: Dec. 10, 2013

(65) Prior Publication Data

US 2015/0045239 A1 Feb. 12, 2015

Related U.S. Application Data

(63) Continuation of application No. 13/462,632, filed on May 2, 2012, now Pat. No. 8,614,087.

(60) Provisional application No. 61/481,592, filed on May 2, 2011.

(51) Int. Cl.
| | |
|---|---|
| *G01N 27/26* | (2006.01) |
| *C12M 1/00* | (2006.01) |
| *C12Q 1/00* | (2006.01) |
| *C12Q 1/68* | (2006.01) |
| *C12M 1/34* | (2006.01) |
| *G01N 27/00* | (2006.01) |
| *G01N 21/00* | (2006.01) |
| *G01N 33/543* | (2006.01) |
| *G01N 27/327* | (2006.01) |
| *B01L 3/00* | (2006.01) |
| *G01N 35/00* | (2006.01) |

(52) U.S. Cl.
CPC ...... *G01N 33/54306* (2013.01); *G01N 27/3273* (2013.01); *B01L 3/502715* (2013.01); *G01N 2035/00158* (2013.01)

(58) Field of Classification Search
CPC .................. G01N 27/3273; G01N 33/54306; G01N 33/543; B01L 3/502715

USPC ............... 204/400, 403.01, 403.02, 403.03; 435/4, 6.1, 283.1, 287.1, 287.2; 422/82.01, 82.05

See application file for complete search history.

(56) References Cited

U.S. PATENT DOCUMENTS

| | | | |
|---|---|---|---|
| 4,739,380 | A | 4/1988 | Lauks et al. |
| 5,004,583 | A | 4/1991 | Guruswamy et al. |
| 5,571,401 | A | 11/1996 | Lewis et al. |
| 7,061,061 | B2 | 6/2006 | Goodman et al. |
| 7,172,897 | B2 | 2/2007 | Blackburn et al. |
| 2003/0073889 | A1 | 4/2003 | Keilbach et al. |
| 2005/0021066 | A1 | 1/2005 | Kuhr et al. |
| 2005/0244811 | A1 | 11/2005 | Soundarrajan et al. |
| 2007/0111202 | A1 | 5/2007 | Henkens et al. |
| 2007/0256941 | A1 | 11/2007 | Prasad et al. |
| 2008/0007296 | A1 | 1/2008 | Umezaki |
| 2008/0262381 | A1 | 10/2008 | Kolen |
| 2010/0109686 | A1 | 5/2010 | Zhe et al. |
| 2010/0179397 | A1 | 7/2010 | Bright et al. |

FOREIGN PATENT DOCUMENTS

| | | |
|---|---|---|
| CN | 1700879 A | 11/2005 |
| CN | 101472940 A | 7/2009 |
| EP | 0706048 A2 | 4/1996 |
| WO | 2005059513 A2 | 6/2005 |

OTHER PUBLICATIONS

International Search Report and Written Opinion for Application No. PCT/US2012/036167, mailed on Jul. 31, 2012, 16 pages.
Non-Final Office Action mailed Mar. 14, 2013 for U.S. Appl. No. 13/462,632, filed May 2, 2012.
Notice of Allowance mailed Nov. 13, 2013 for U.S. Appl. No. 13/462,632, filed May 2, 2012.
Supplementary European Search Report for Application No. EP12779771, mailed on Aug. 27, 2014, 7 pages.
First Office Actiom mailed Oct. 30, 2014 for Chinese Application No. 201280033059 filed May 2, 2012.

*Primary Examiner* — Narayan Bhat
(74) *Attorney, Agent, or Firm* — David A. Casimir; Casimir Jones, S.C.

(57) ABSTRACT

Provided herein is technology relating to testing biological samples and particularly, but not exclusively, to methods for performing multiple, simultaneous real-time assays on a sample in a single-use disposable format. For example, the technology relates to methods employing an apparatus that finds use, for example, for point-of-care diagnostics, including use at accident sites, emergency rooms, in surgery, in intensive care units, as well as for non-medical applications.

17 Claims, 5 Drawing Sheets

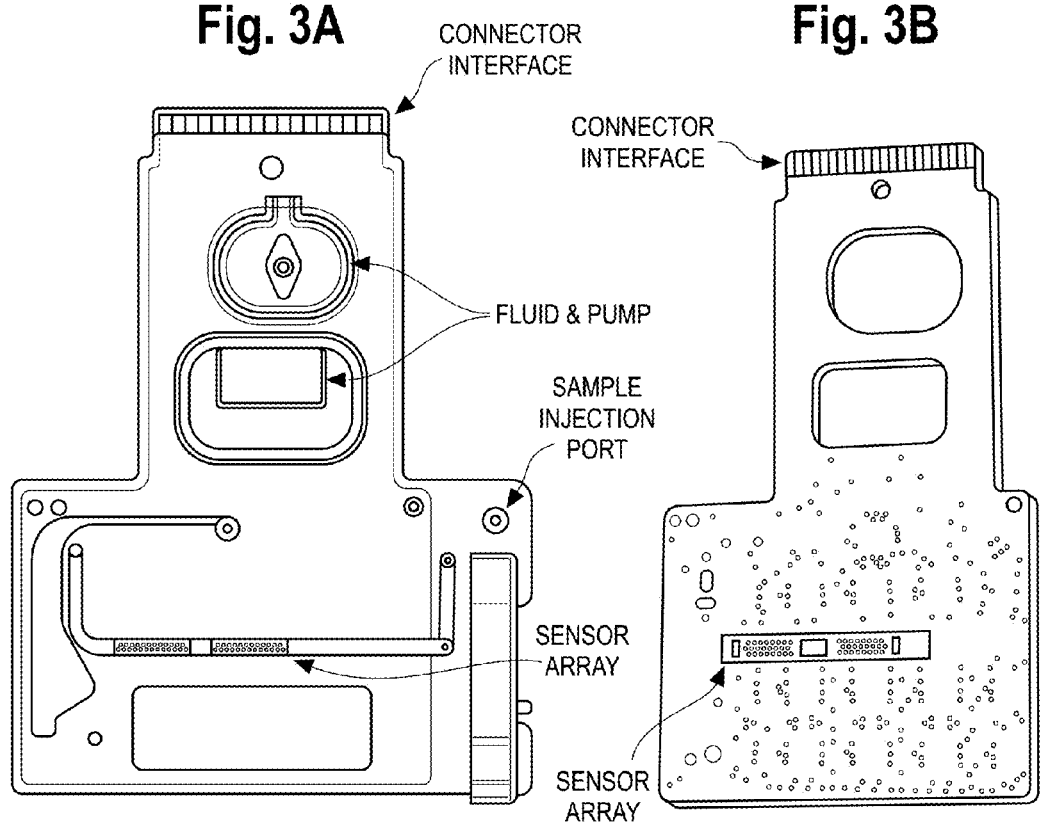

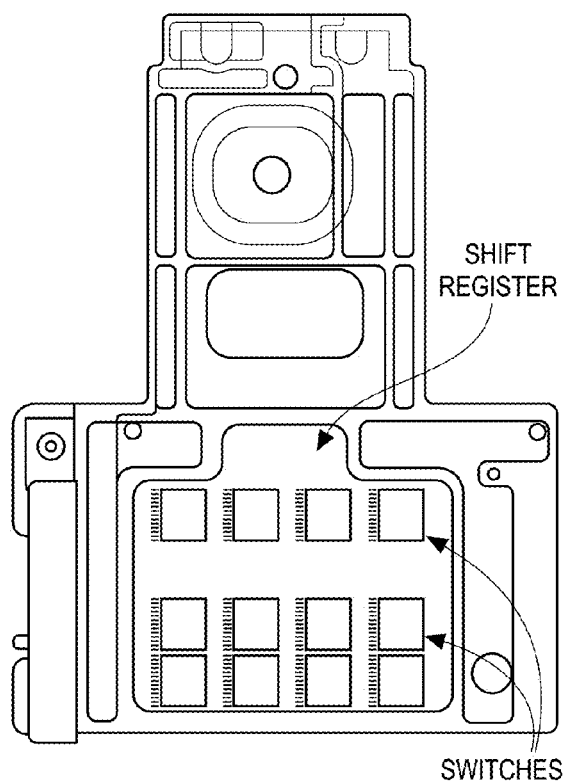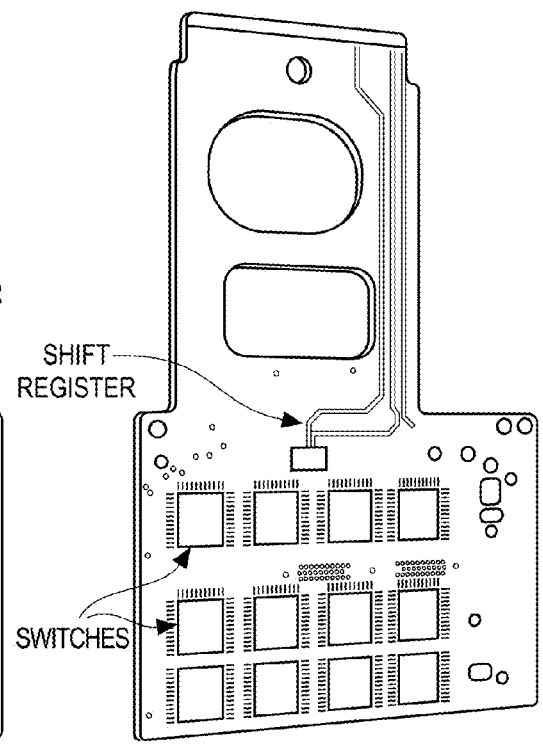

US 9,097,711 B2

MULTIPLE-ANALYTE ASSAY DEVICE AND SYSTEM

CROSS-REFERENCE TO RELATED APPLICATION

The present Application is a continuation of U.S. application Ser. No. 13/462,632, filed May 2, 2012, which claims priority to U.S. Provisional Application Ser. No. 61/481,592 filed May 2, 2011, the entirety of which is herein incorporated by reference.

FIELD OF INVENTION

Provided herein is technology relating to testing biological and/or environmental samples. In particular, the technology is related to devices, systems, and kits for performing multiple, simultaneous real-time assays on a sample. For example, the technology relates to a system for use in point-of-care diagnostics, including use at accident sites, emergency rooms, in surgery, in intensive care units, as well as for non-medical applications.

BACKGROUND

Numerous laboratory tests for analytes of interest are performed on biological or environmental samples for diagnosis, screening, disease staging, forensic analysis, pregnancy testing, drug testing, and other reasons. However, most of these quantitative tests require the expertise of trained technicians in a laboratory setting using sophisticated instruments. Moreover, laboratory testing increases the cost of analysis and delays the results. In many circumstances, delay can be detrimental to a patient's condition or prognosis, such as, for example, the analysis of markers indicative of myocardial infarction. In these critical situations and others, it would be advantageous to perform such analyses at the point of care, accurately, inexpensively, and with a minimum of delay.

Some solutions to this problem have been developed, for example, using a disposable cartridge configured to analyze a single analyte and a portable, handheld reading apparatus configured to accept the cartridge, process the data, and present data to a user (see, e.g., U.S. Pat. Nos. 7,419,821 and 5,096,669, herein incorporated by reference in their entireties). These conventional cartridges have a single input and a single output for communicating with the reader, e.g., to transmit and receive signals for controlling the analysis and transferring the resulting data. However, many molecular tests require (or would benefit from) assessing the presence or absence of, or measuring the amount or concentration of, multiple analytes. These tests require multiple analyte sensors, each adapted to test for a single analyte in the multiple analyte panel. While cartridges can be manufactured to comprise multiple sensors for testing multiple analytes, the data collection requires obtaining real-time signals from each individual sensor. A solution to this problem would be to design cartridges and readers to have multiple communication channels, one for each sensor or analyte being tested. However, such a solution is not desirable for several reasons. First, such redesigning may require changes in the form factor (e.g., dimensions and size of the cartridges and/or reader) and/or the electronics of both the cartridges and the reading apparatus. These changes may then, in turn, require costly adjustments in manufacturing the devices and/or produce resistance among users in accepting the new system. Second, while the disposable cartridges are relatively inexpensive, the reading apparatus is relatively expensive. Thus, users will not want to purchase a new reading device to accommodate the multiple-analyte cartridges. Accordingly, the field has a need for a testing technology that provides point-of-care, real-time testing of multiple analytes using the prior installed base of reading apparatuses that comprise one input and one output channel.

SUMMARY

To address this problem, provided herein is technology relating to testing multiple analytes in biological samples. In particular, herein are provided devices, systems, and kits for performing multiple, simultaneous real-time assays on a sample in a single-use disposable format, although other formats may also be used. For example, the technology relates to an apparatus that finds use, for example, in point-of-care diagnostics, including use at accident sites, emergency rooms, in surgery, in intensive care units, as well as for non-medical applications. The technology comprises a disposable cartridge having one or more analyte sensors, a reading apparatus adapted to receive the cartridge, and component for the reader to control and/or communicate with the multiple sensors over a single output and a single input channel, although additional channels may be used if desired.

Accordingly, in some embodiments, the technology provided herein relates to a cartridge for sensing an analyte in a sample, the cartridge comprising a plurality of analyte sensors for assaying the sample; a multiplexer electronically connected to the plurality of analyte sensors; and a data output electronically connected to the multiplexer, wherein the multiplexer receives a plurality of data signals from the plurality of analyte sensors; encodes an output signal comprising a portion of a data signal received during a timeslot; and transmits the output signal to the data output. In some embodiments, the cartridge further comprises an interface for connecting the cartridge to a reading apparatus. In various embodiments, the interface comprises any of a number of different communication mechanisms; for example, in some embodiments the interface comprises an electrical connection and in some embodiments the interface comprises a mechanical connection. The interface, in some embodiments, transmits signals between the cartridge and the reading apparatus. In specific embodiments, the electrical connection is a connector chip.

The technology provides a device comprising a multiplexer for receiving, transmitting, and processing data and output signals. In some embodiments, the multiplexer is a time-division multiplexer. In some embodiments, the data signal is a continuous data signal and the output signal is a discrete signal. Furthermore, in some embodiments the output signal is produced by digitally sampling a data signal, e.g., during a timeslot of, for example, 0.01-0.1 seconds, 0.1-1 seconds, or 1-10 seconds. The timeslot can be determined by any suitable component or method. For example, in some embodiments, a clock determines the timeslot and in some embodiments the control input determines the timeslot. Data can be transmitted in a variety of ways—for example, in some embodiments, the output signal comprises a plurality of channels wherein each channel comprises a portion of a data signal received during a timeslot.

The cartridge comprises multiple analyte sensors for detecting and/or measuring multiple analytes. For example, in some embodiments the cartridge comprises 10-100 analyte sensors, although both higher and lower numbers are contemplated. The multiplexer is configured to process and route signals from the multiple sensors. In some embodiments, the multiplexer selects which data signal received from the plurality of analyte sensors is encoded and routed. Moreover, in some embodiments, the multiplexer also calculates a function from the multiple data signals, and, accordingly, in some embodiments of the technology, the output signal comprises a function calculated from a plurality of data signals received from the plurality of analyte sensors. In some embodiments, the data collected individually and/or collectively finds use in informing a medical diagnosis. In some embodiments the output signal indicates the presence of a medical condition in a subject and in some embodiments the output signal indicates the absence of a medical condition in a subject.

In some embodiments the multiplexer is used to route a data signal from the analyte sensors to the output and, in some embodiments, to the reading apparatus. There are many ways in which the signals are processed; encoded; decoded; transmitted; transformed; and/or are selected for processing, encoding, decoding, transmission, or transformation. For example, in some embodiments, the control input provides a signal to the multiplexer indicating which data signal received from the plurality of analyte sensors is encoded and routed. In some embodiments, the cartridge further comprises a demultiplexer electronically connected to the plurality of analyte sensors and an input electronically connected to the demultiplexer. The technology provides in some embodiments that the demultiplexer receives an input signal from the input; decodes the input signal into a control signal; and routes the control signal to an analyte sensor. The control signal provides information and/or controls the multiplexer and/or the analyte sensors. For example, in some embodiments the control signal initiates a transmission of a data signal from an analyte sensor and in some embodiments the control signal terminates a transmission of a data signal from an analyte sensor. In some embodiments, the control signal determines the timeslot.

The technology provides for multiplexed communications. As such, in some embodiments data from multiple sensors is transmitted in a multiplexed format over a single output. In some embodiments, the multiplexing is performed in the time domain; accordingly, in some embodiments, a data signal is transmitted from an analyte sensor during a timeslot, for example, in some embodiments, a timeslot of 0.01-0.1 seconds, of 0.1-1 seconds, or of 1-10 seconds.

In some embodiments, the devices (e.g., a disposable cartridge) find use in systems configured for sensing an analyte in a sample. Therefore, there are appropriately provided herein embodiments comprising embodiments of the cartridges described and an appropriate reading apparatus. In certain embodiments of the systems provided herein, the cartridge comprises an analyte sensor configured to analyze a sample; a multiplexer configured to receive a data signal, encode an output signal, and route the output signal; and a first interface component configured to mate with the reading apparatus and communicate with the reading apparatus; and wherein the reading apparatus comprises a second interface component configured to mate with the cartridge and communicate with the cartridge; and a microprocessor configured to decode the output signal. The data signal carries data from the electrochemical sensors to the reading apparatus. In some embodiments, the signal decoded by the microprocessor (e.g., the decoded output signal) comprises the data signal or a transformation of the data signal.

Embodiments of the system are configured for interfacing with a user—e.g., to receive input from the user and/or to transmit data or other information to the user. Accordingly, in some embodiments the system further comprises a user interface.

The system provides a technology to test multiple analytes in a sample. For example, some embodiments provide that the system comprises a cartridge comprising a plurality of analyte sensors. In some embodiments, the multiplexer is further configured to calculate a function from a plurality of data signals received from the plurality of analyte sensors, said output signal comprising the function. And, in some embodiments of the system, the microprocessor is further configured to calculate a function from a plurality of data signals received from the plurality of analyte sensors. The systems provided herein find use in aiding a medical diagnosis. As such, in some embodiments, the decoded output signal indicates the presence of a medical condition in a subject and in some embodiments the decoded output signal indicates the absence of a medical condition in a subject.

The devices and systems are provided in kits for convenient use by a user. Some embodiments therefore provide a kit comprising embodiments of the cartridge described herein and an instruction for use. Additionally, some embodiments further comprise an apparatus for collecting a sample from a subject. Kits may also comprise analysis software or any other components useful, necessary, or sufficient for conducting the desired analysis.

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings:

FIG. 3 shows top (A and C) and bottom (B and D) views of an embodiment of the multiplex cartridge technology provided herein. FIG. 3A is a drawing showing a top view of the cartridge and FIG. 3B is a top view of the PCB board; FIG. 3C is a drawing showing a bottom view of the cartridge and FIG. 3D is a bottom view of the PCB board.

DETAILED DESCRIPTION

Figure 1A:
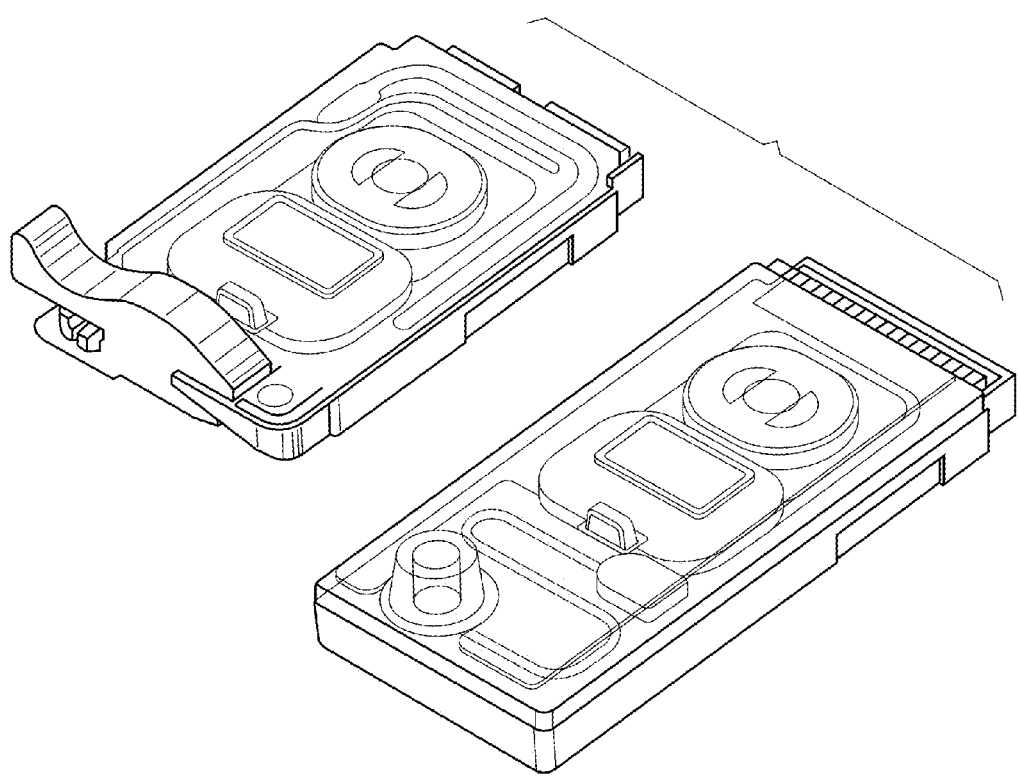
FIG. 1 is a panel of drawings showing a perspective (A) and a top view (B) of embodiments of the cartridges provided herein.

The technology provided herein provides devices, systems, kits and related technologies associated with a multiple analyte sensor cartridge and, in some embodiments, a reading apparatus adapted to accept and interface with the cartridge. The cartridge comprises a multiplexer for receiving data from the multiple sensors and transmitting the data to a data output. Such technology finds use, for example, in the field of medical diagnostics for performing tests requiring the analysis of more than one analyte.

DEFINITIONS

To facilitate an understanding of the present technology, a number of terms and phrases are defined below. Additional definitions are set forth throughout the detailed description.

As used herein, "a" or "an" or "the" can mean one or more than one. For example, "a" widget can mean one widget or a plurality of widgets.

As used herein, a "signal" is a time-varying quantity associated with one or more properties of a sample that is assayed. A signal can be continuous in the time domain or discrete in the time domain. As a mathematical abstraction, the domain of a continuous-time signal is the set of real numbers (or an interval thereof) and the domain of a discrete-time signal is the set of integers (or an interval thereof). Discrete signals often arise via "digital sampling" of continuous signals. For example, an audio signal consists of a continually fluctuating voltage on a line that can be digitized by reading the voltage level on the line at a regular interval, e.g., every 50 microseconds. The resulting stream of numbers is stored as a discrete-time digital signal.

As defined herein, the term "light" refers to a form of energy transmission through a vacuum or a medium in which electric and magnetic fields are propagated as waves. Further, it includes visible light, infrared, and ultraviolet. The light may comprise a single wavelength or a number of wavelengths. The wavelength or wavelengths may be within the visible spectrum, outside the visible spectrum (e.g., in the infrared or ultraviolet), or a combination thereof. While "light" is electromagnetic radiation of a wavelength that is visible to the human eye (in a range from about 380 or 400 nanometers to about 760 or 780 nanometers), the term "light" is used herein to mean electromagnetic radiation of any wavelength, whether visible or not.

As used herein, "light source" refers to a process by which light enters a system. For example, in some applications, the light source is a laser. The source may produce broadband or one or more distinct wavelengths. Further, the source may output energy in single or multiple shots or impulses of energy or may scan through a series or continuum of wavelengths.

As used herein, the terms "subject" and "patient" refer to any animal, such as a dog, a cat, a bird, livestock, and particularly a mammal, and preferably a human.

As used herein, the term "sample" is used in its broadest sense. In one sense, it is meant to include a representative portion or culture obtained from any source, including biological and environmental sources. Biological samples may be obtained from animals (including humans) and encompass fluids, solids, tissues, and gases. Biological samples include blood products, such as plasma, serum, and the like. Environmental samples include environmental material such as surface matter, soil, mud, sludge, biofilms, water, and industrial samples. Such examples are not however to be construed as limiting the sample types applicable to the present invention.

As used herein, the term "analyte" is to be construed broadly as any compound, molecule, or other substance of interest to be detected, identified, or characterized.

As used herein, the term "sensor" refers to an ambient sensing device such as, for example, ion sensitive and chemical sensitive devices that generate an electrical signal (e.g., current, potential, or conductivity) based on the presence of or concentration of an analyte in the sample being tested.

EMBODIMENTS OF THE TECHNOLOGY

Although the disclosure herein refers to certain illustrated embodiments, it is to be understood that these embodiments are presented by way of example and not by way of limitation.

1. Cartridges

The present technology provides a disposable cartridge for performing assays on samples. The cartridge comprises one or more analyte sensors (e.g., an electrochemical analyte sensor and including, in some embodiments, one or more reference sensors), one or more chambers for holding fluids or other sample types, and a multiplexer for processing signals received from the analyte sensors and sending data signals to an output, and in some embodiments, to a reading apparatus. In some embodiments the cartridge comprises a demultiplexer receiving signals from the reading apparatus and routing signals to the analyte sensors. The cartridge further comprises fluid handling components (e.g., inlet ports, outlet ports, metering components to measure and provide specific volumes of fluids, and conduits for handling and transporting the sample and other fluids) and the necessary electronic connections for sending and receiving electronic signals among the multiplexer, demultiplexer, the reading apparatus, and the analyte sensors.

The cartridge is adapted for insertion into a reading apparatus and accordingly has a plurality of mechanical and electrical connections for physically and electrically interfacing with the reading apparatus. Furthermore, in some embodiments the cartridge comprises one or more chambers in which is stored a fluid for, e.g., washing the sensors, providing a substrate for an analysis (e.g., to measure an enzyme activity), providing a standard or reference for an analysis, or providing some other fluid (e.g., a buffer, an amending solution, or some other solution) that is required for the analysis. In an embodiment of the cartridge, the fluid is stored in a foil pack and, upon insertion of the cartridge into a reading apparatus, a gasket transmits pressure onto the fluid-containing foil pack, rupturing the package upon a spike and expelling the fluid into a conduit for washing the sensors prior to performing a measurement.

Figure 1B:
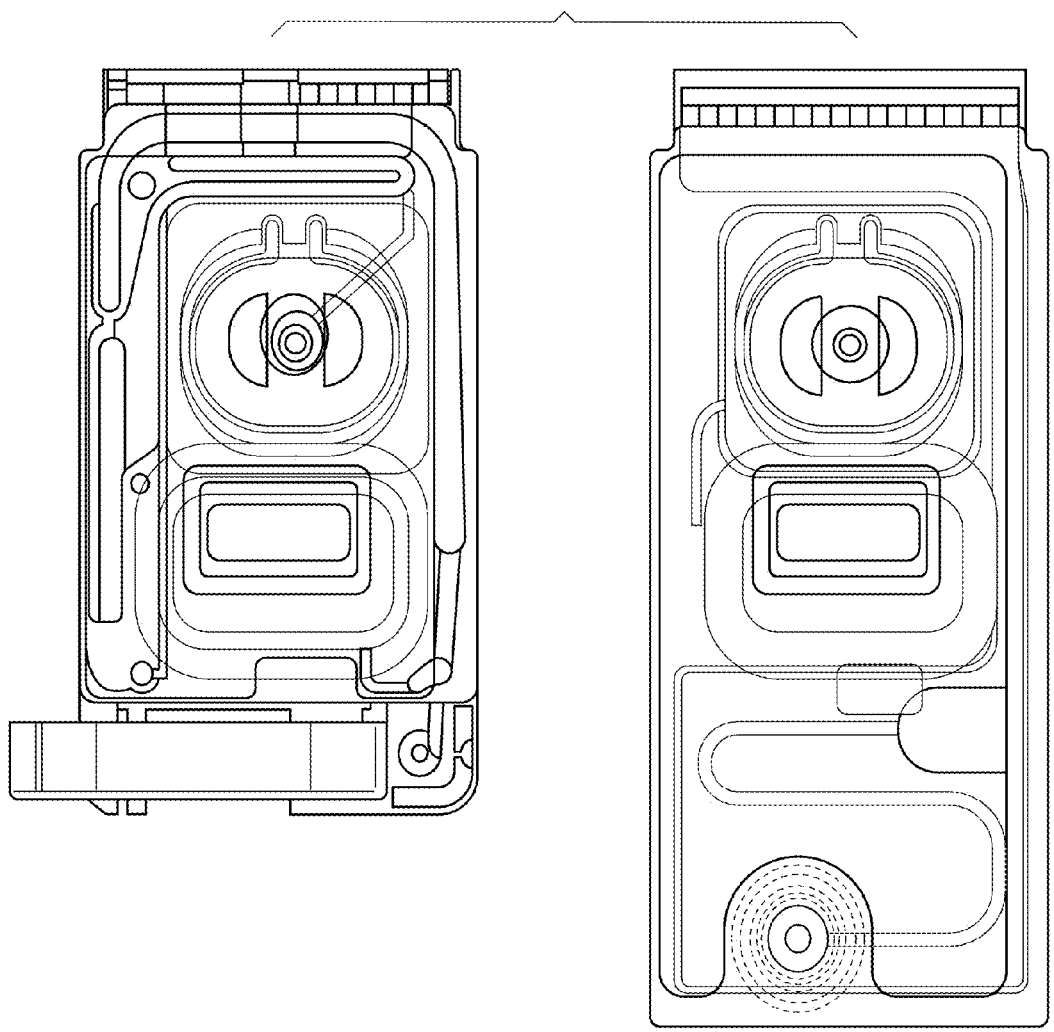
Figure 2:
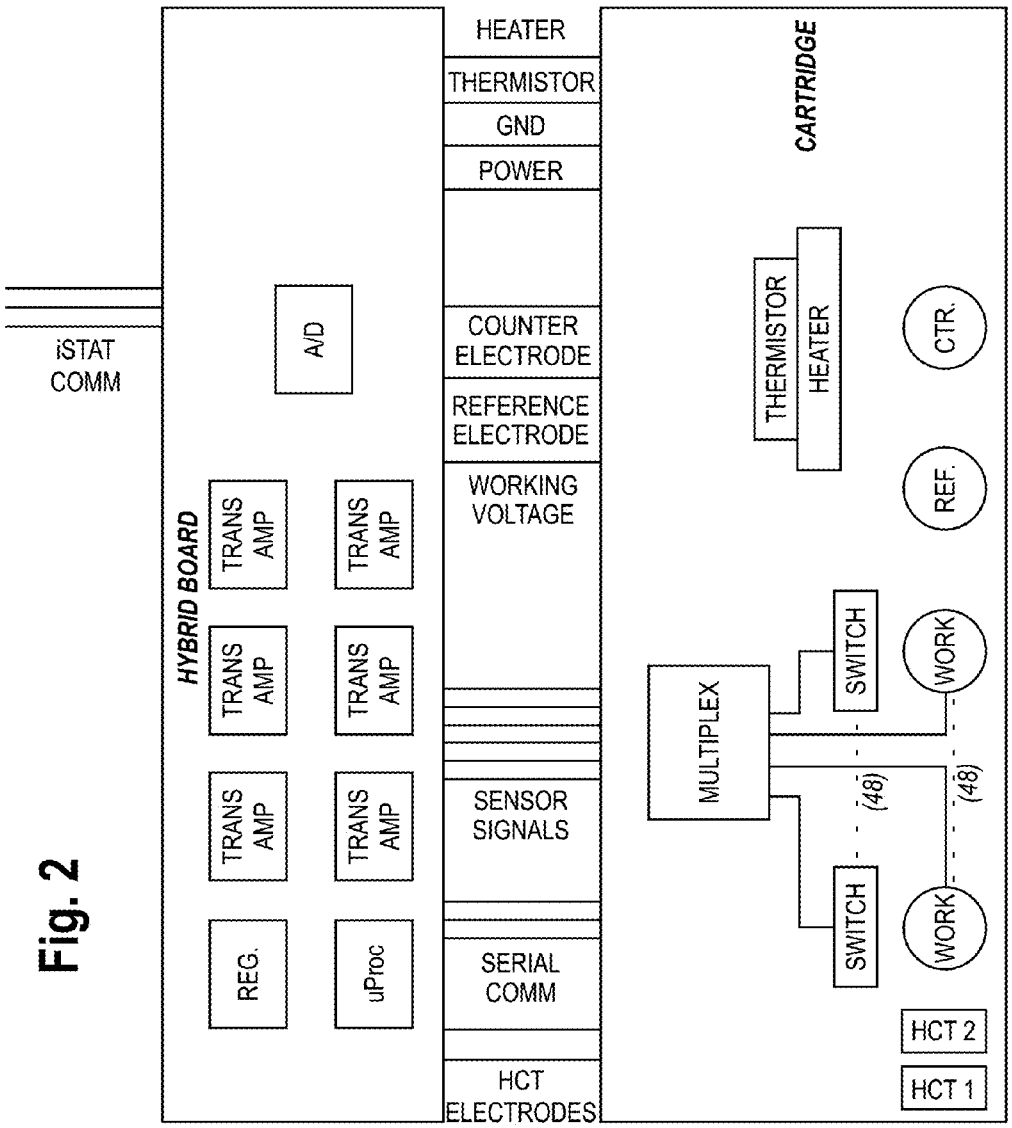
FIG. 2 is a schematic drawing showing an embodiment of the multiplex device comprising a cartridge printed circuit board unit connected by an 18-pin connector to a hybrid printed circuit board, which is in communication with a handheld apparatus by a serial communication interface.

Embodiments of the cartridges take many forms and configurations and they are constructed from many suitable materials. For example, U.S. Pat. No. 7,419,821, incorporated herein in its entirety for all purposes, provides an example of a single-use cartridge. Furthermore, a disposable sensing device for measuring analytes in a blood sample is disclosed in U.S. Pat. Nos. 5,096,669; 6,750,053; 7,723,099. Other devices are disclosed in U.S. Pat. Nos. 5,628,961 and 5,447,440 for measuring clotting time. These devices employ a reading apparatus and a cartridge that fits into the reading apparatus for the purpose of measuring analyte concentrations and viscosity changes in a blood sample as a function of time. Embodiments of the cartridges described are provided in the drawings of FIG. 1.

In some embodiments, the cartridges are used with a single sample. The use of such cartridges provides a convenient way to test samples while minimizing sample contamination and sample carry-over risks. Appropriately, in some embodiments, the cartridges are disposable.

2. Multiplexer

The technology provided herein comprises a multiplexer. A multiplexer selects one of several analog or digital input signals and forwards the selected input into a single line (e.g., an output). Accordingly, multiplexing is a method by which multiple signals are combined into one signal over a shared medium, e.g., transmitted over a physical transmission medium. An electronic multiplexer makes it possible for several signals to share one device or resource, e.g., an output channel. As such, a multiplexer can be considered to be a multiple-input, single-output switch. Multiplexing divides the capacity of the low-level communication channel into several higher-level logical channels, one for each message signal or data stream to be transferred.

Similarly, a demultiplexer performs the reverse process, known as demultiplexing, to extract multiple channels from a multiplexed signal. A demultiplexer may be paired with a multiplexer so that the demultiplexer decodes the multiplexed signal encoded and transmitted by the multiplexer. A demultiplexer also provides a technology to send multiple efferent output signals from a single efferent input signal.

Time-division multiplexing is a type of multiplexing in which two or more signals or are transferred apparently simultaneously as sub-channels in one communication channel, but are physically taking turns on the channel. The time domain is divided into several recurrent timeslots of fixed length, one for each sub-channel. A portion (e.g., a digital sample, byte, or data block) of sub-channel 1 is transmitted during timeslot 1, a portion (e.g., a digital sample, byte, or data block) of sub-channel 2 during timeslot 2, etc. In some embodiments, one time-division multiplexed frame comprises one timeslot per sub-channel and a synchronization channel. Furthermore, in some embodiments, one time-division multiplexed frame sometimes comprises an error correction channel before the synchronization. After the last sub-channel, error correction, and synchronization channels, the cycle repeats with a new frame, starting with the second portion (e.g., digital sample, byte, or data block) from sub-channel 1, etc. If done sufficiently and quickly, the receiving devices will not detect that some of the circuit time was used to serve another logical communication path.

3. Sensors

The multiplexer processes and routes signals received from a plurality of analyte sensors. In some embodiments, the sensors are electrochemical analyte sensors. The electrochemical analyte sensors are exposed to and react with the sample to be assayed and generate an electrical signal (e.g., a potential, a current, a conductivity) that is a function of the chemical activity of the analyte being measured. For example, in some embodiments the electrochemical analyte sensor generates a potential that is a function of the amount or concentration of the analyte in the sample (e.g., a potentiometric sensor). While not limited in the types of sensors that may be used, it is contemplated that the device comprises microfabricated sensors suitable for mass production and capable of detecting a wide range of biological molecules. Examples of such electrochemical analyte sensors are provided in U.S. Pat. Nos. 4,613,422; 4,739,380; 4,933,048; 5,063,081; 5,200,051; 5,837,446; 5,837,454; 6,030,827; 6,379,883; 7,540,948; including reference sensors in U.S. Pat. No. 7,723,099, all of which are incorporated herein by reference in their entireties for all purposes.

In particular embodiments of the present invention, the transduction of the analyte concentration into a processable signal is by an electrochemical component. These transducers may include amperometric, potentiometric (voltammetric), or conductimetric sensors. However, the technology may comprise other types of transducers (e.g., acoustic wave sensing devices, thermistors, gas-sensing electrodes, field-effect transistors, optical and evanescent field wave guides, and the like). A useful discussion and tabulation of transducers which may be exploited in a sensor as well as the kinds of analytical applications in which each type of transducer or sensor, in general, may be utilized is found in Trends in Biotech. 2(3): 59-65 (1984), the disclosures and descriptions contained therein are incorporated by reference herein for all purposes. Of the three electroanalytical techniques mentioned earlier, the potentiometric and amperometric techniques are preferred because the output signal may most easily be related directly to the response of the sensor to a particular analyte.

In some embodiments the electrochemical analyte sensor is used to detect and/or quantify an immunoactive analyte. The analysis scheme for the detection of low concentrations of an immunoactive analyte relies on the formation of an enzyme-labeled antibody/analyte/surface-bound antibody "sandwich" complex. The concentration of analyte in a sample is converted into a proportional surface concentration of an enzyme. The enzyme is capable of amplifying the analyte's chemical signal by converting a substrate to a detectable product. For example, where alkaline phosphatase is the enzyme, a single enzyme molecule can produce several thousand detectable molecules per minute, improving by several orders of magnitude the detectability of the analyte compared to schemes in which a detectable species is attached to the antibody in place of alkaline phosphatase.

In some embodiments of this detection technology, the sensors detect an electrogenic species. The electrogenic species is a chemical, moiety, or composition that is not electroactive until an enzyme converts it into an electroactive species. The inactive species is provided in the sample reaction mixture and conversion to the active form is associated with, and thus indicative of, a property of the analyte (e.g., concentration, conformation, amount, oligomerization state, binding state, etc.). For example, in some embodiments the electrogenic species is a ferrocene derivative, p-aminophenol, hydrogen peroxide, and/or ammonium ion. It is to be understood that these examples are demonstrative and the technology is not limited in the electrogenic species that finds use in the sensor. Furthermore, in some embodiments an enzyme produces the electrogenic species. Examples of enzymes that produce electrogenic species include, but are not limited to, alkaline phosphatase, glucose oxidase, lactate oxidase, glutamate oxidase, choline oxidase, cholesterol oxidase, alcohol oxidase, amyloglucosidase oxidase, lysine oxidase, L-amino acid oxidase, ascorbate oxidase, galactose oxidase, and urease. In some embodiments, the electrogenic species is derived from an enzyme reaction associated with nucleotide capture.

In immunosensor embodiments, it is advantageous to contact the sensor first with a sample and then with a wash fluid prior to recording a response from the sensor. In specific embodiments, the sample is amended with an antibody-enzyme conjugate that binds to the analyte of interest within the sample before the amended sample contacts the sensor. Binding reactions in the sample produce an analyte/antibody-enzyme complex. The sensor comprises an immobilized antibody to the analyte, attached close to an electrode surface. Upon contacting the sensor, the analyte/antibody-enzyme complex binds to the immobilized antibody near the electrode surface. It is advantageous at this point to remove from the vicinity of the electrode as much of the unbound antibody-enzyme conjugate as possible to minimize background signal from the sensor. The enzyme of the antibody-enzyme complex is advantageously capable of converting a substrate, provided in the fluid, to produce an electrochemically active species. This active species is produced close to the electrode and provides either a current from a redox reaction at the electrode when a suitable potential is applied (amperometric operation). Alternatively, if the electroactive species is an ion, it can be measured potentiometrically. In amperometric measurements the potential may either be fixed during the measurement or varied according to a predetermined waveform. For example, a triangular wave can be used to sweep the potential between limits, as is used in the well-known technique of cyclic voltammetry. Alternatively, digital techniques such as square waves can be used to improve sensitivity in the detection of the electroactive species adjacent to the electrode. From the current or voltage measurement, the amount or presence of the analyte in the sample is calculated. These and other analytical electrochemical methods are well known in the art.

In one aspect, the technology provided herein provides a sensor comprising a capture element and/or a capture reagent.

Such elements are molecules, moieties, substances, or compositions that preferentially (e.g., specifically and selectively) interact with a particular target sought to be isolated and purified. Any capture element having desired binding affinity and/or specificity to the analyte target can be used in the present technology. For example, the capture element can be a macromolecule such as a peptide, a protein (e.g., an antibody or receptor), an oligonucleotide, a nucleic acid, (e.g., nucleic acids capable of hybridizing with the target nucleic acids), vitamins, oligosaccharides, carbohydrates, lipids, or small molecules, or a complex thereof. As illustrative and non-limiting examples, an avidin target capture element may be used to isolate and purify targets comprising a biotin moiety, an antibody may be used to isolate and purify targets comprising the appropriate antigen or epitope, and an oligonucleotide may be used to isolate and purify a complementary oligonucleotide (e.g., a poly-dT oligonucleotide may be used to isolate and purify targets comprising a poly-A tail).

Any nucleic acids, including single-, double-, and triple-stranded nucleic acids, are contemplated as targets for capture (e.g., the product of an amplification reaction (e.g., PCR, RT-PCR, TMA, NASBA, and the like); a genome or genomic fragment; a restriction fragment; an RNA (e.g., a tRNA; an mRNA; a microRNA; an siRNA an rRNA); a chromosome; a plasmid; a viral genome; a primer; a gene). Many kinds of compositions and/or moieties serve as a capture element. For example, a biotin-labeled nucleic acid can be captured using an avidin capture element or a nucleic acid comprising a poly-A tail can be captured by a poly-dT capture element. In some embodiments, a nucleic acid serves as the capture element. Any nucleic acid, including single-, double-, and triple-stranded nucleic acids, that are capable of binding, or specifically binding, to the target can be used as the capture element in the present device. Examples of such nucleic acids include DNA, such as A-, B- or Z-form DNA, and RNA such as mRNA, tRNA and rRNA, aptamers, peptide nucleic acids, and other modifications to the sugar, phosphate, or nucleoside base. Thus, there are many strategies for capturing a target and accordingly many types of capture elements are known to those in the art. While not limited in the mode by which a target nucleic acid can be captured, some embodiments of the technology provided herein comprise using an oligonucleotide that is complementary to the target and that thus captures the target by specifically and selectively hybridizing to the target nucleic acid. Other embodiments use other capture strategies, e.g., an antibody.

In addition, target capture elements comprise a functionality to localize, concentrate, aggregate, etc. the capture element and thus provide a way to isolate and purify the target when captured (e.g., bound, hybridized, etc.) to the capture element, e.g., when a target:capture element complex is formed. For example, in some embodiments the portion of the target capture element that interacts with the target (e.g., the oligonucleotide) is linked to a solid support (e.g., a bead, surface, resin, column). Often, the solid support allows the use of a mechanical technology to isolate and purify the target:capture element complex from a heterogeneous solution.

Also contemplated are embodiments wherein the sensor is a light sensor (e.g., a photodetector). The light sensor detects light and produces an electrical signal (e.g., a potentiometric, amperometric, or conductimetric signal). The light is related to a property or characteristic of the analyte measured in the assay (e.g., concentration, pH, conformation, activity, binding state, redox state, oligomerization state, amount, etc.). The light detected is produced by a number of sources and processes. For example, some assays of an analyte produce light by fluorescence or luminescence (e.g., bioluminescence) and some assays comprise the use of a quantum dot and the quantum dot produces light. In some assays, the light is detected after passing through the sample (e.g., in an assay (e.g., a spectrophotometric assay) that measures the transmittance or absorbance of the sample).

The light sensor can be configured in any way that allows monitoring the optical properties of the sample and/or an analyte. For example, some embodiments provide that the sensor monitors light intensity. In embodiments used for spectrometry, the sensor detects light at a wavelength that is about the same wavelength as the wavelength that is incident on the sample and/or analyte. In fluorescence detection embodiments, the sensor monitors light intensity at a wavelength that is longer than the wavelength that is incident on the sample and/or analyte. The sensor comprises any suitable technology to measure optical properties. For example, in some embodiments the sensor is a spectrometer. Additional embodiments provide that the sensor is a photoresister, a photovoltaic cell, a photodiode, a photomultiplier tube, a photocathode, a phototransister, a charge-coupled device, or a reverse-biased LED. In some embodiments, the sensor monitors one or more wavelengths and in some embodiments the photodetector records a spectrum.

4. Analytes and Samples

The technology is useful for the convenient and real-time detection and quantitative measurement of any number of diverse analyte species. For example, types or classes of analytes include, but are not limited to, ionophores, ion exchangers, enzymes, biochemical metabolites, biological ions, respiratory gases, antibodies, antigens, lectins, neurochemical receptors, crystals, polypeptides, nucleic acids (e.g., oligonucleotides, polynucleotides, nucleotides, nucleosides, molecules of DNA, molecules of RNA), proteins, prions, toxins, peptides, sugars, lipids, steroids, salts, ions, glycoproteins, metalloproteins, cofactors, immunoglobulins, and other macromolecules of physiological significance including mixtures or active fragments or subunits thereof. An analyte may be present in an isolated form or in a complex with other substances. In addition, an analyte may be associated with a cell, a tissue, a microorganism (e.g., living, dead, or a lysate or other composition derived therefrom), a virus, or other biological material or composition derived therefrom. Accordingly, the analyte is useful in some embodiments, for example, in detecting the presence of a microorganism, a virus, or a particular cell type (e.g., a cancer cell, a tissue type) in a sample.

Examples of particular useful analytes include, but are not limited to, cTnI, CK-MB, bNP, TSH, hCG, PSA, adrenocorticotropic hormone, antinuclear, thyroglobulin, antithyroid, antithyroid peroxidase, and markers associated with hepatitis, rheumatoid factor, Alzheimers disease, atherosclerosis, and the like.

The technology is useful in the detection of viruses, for example, HIV, HTLV, adenoviruses, herpesviruses, poxviruses, parvoviruses, picorinoviruses, togaviruses, orthomyxoviruses, rhabdoviruses, retroviruses, and hepadnaviruses, among others. Also, the technology is useful in detecting the causative agents, or markers associated with, prion-related diseases such as scrapie, chronic wasting disease, and bovine spongiform encephalopathy.

The present technology is useful for the analysis of most liquid samples including undiluted biological samples such as whole blood, lymph, plasma, serum, saliva, urine, stool, perspiration, mucus, tears, cerebrospinal fluid, nasal secretion, cervical or vaginal secretion, semen, pleural fluid, amniotic fluid, peritoneal fluid, middle ear fluid, joint fluid, gastric aspirate or the like. It should also be understood that solid or dessicated samples may be dissolved in an appropriate solvent to provide a liquid mixture suitable for analysis. Multiplex assays may include collections of similar analytes (e.g., different nucleic acid molecules from a range of different organisms) or different analytes (e.g., a nucleic acid with a peptide with a small molecule, etc.).

U.S. Pat. No. 5,063,081 provides a detailed discussion and experimental data for several exemplary sensors adapted for use in detecting clinically relevant analytes: glucose, base, blood urea nitrogen, uric acid, IgG, theophylline, cholesterol, adenosine-5-triphosphate (ATP), creatinine, potassium ion, chloride ion, sodium ion, pH, and the like. A particularly useful embodiment comprises ligand/ligand receptor-based biosensors adapted for performing analyses based upon intermolecular affinity and/or immunochemical complex interactions. A ligand/ligand-receptor-based assay may be devised in which one or the other member of the complex may be the analyte species of interest and the other component may be used as the sensor-immobilized ligand receptor or immunoreactive species. Accordingly, ligand/ligand receptor-based assays are adaptable to measure a broad range of analytes (e.g., antigen/antibody, antibody/anti-antibody, biotin/avidin, immunoglobulin G/protein A, enzyme/enzyme receptor, ion/chelator, hormone/hormone receptor, substrate/enzyme, DNA (or RNA)/complementary polynucleotide sequence, drug/drug receptor, and the like). It is particularly contemplated that the sensors are adapted to assay an analyte by an immunoassay.

The technology provided herein finds use in the medical, clinical, and emergency medical fields. Accordingly, in some embodiments the device is used to assay biological samples. In such an assay, the biological sample comprises the analyte and measuring a property of the analyte is indicative of a state or a property of the sample and, in some embodiments, the subject from which the sample was taken. Some relevant samples include, but are not limited to, whole blood, lymph, plasma, serum, saliva, urine, stool, perspiration, mucus, tears, cerebrospinal fluid, nasal secretion, cervical or vaginal secretion, semen, pleural fluid, amniotic fluid, peritoneal fluid, middle ear fluid, joint fluid, gastric aspirate, a tissue homogenate, a cell homogenate, or the like. For example, for a subject who has diabetes, the sample is a blood sample and the analyte to be measured is glucose (e.g., glucose concentration).

Furthermore, in some embodiments the sample comprises or is suspected to comprise a composition associated with bioterrorism, e.g., a biological and/or chemical agent. A biological agent is, or is derived from, a living, typically pathogenic, biological organism (e.g., a bacterium, a virus, a eukaryote such as a fungus or a parasite). In some embodiments the sample comprises a biological toxin or other substance derived from a biological source (e.g., a small molecule, a protein, a prion). Bioterrorism agents are, or are derived from, biological sources; thus, particular biological signatures can be used to detect them, e.g., nucleic acids, proteins, or other small molecules that identify the biological agent and that can be detected by an appropriate assay, e.g., by an electrochemical analyte sensor. For example, an electrochemical analyte sensor can be used to detect a PCR amplicon, a virulence factor (e.g., a gene or protein), a toxin or genes encoding the production of a toxin, and/or markers associated with drug resistance.

Biological agents, some of military importance include, but are not limited to, *Bacillus anthracis* (causative agent of anthrax); *Staphylococcus* spp.; *Brucella abortus, Brucella melitensis*, and *Brucella suis* (causative agents of brucellosis); *Vibrio cholerae* (causative agent of cholera); *Corynebacterium diphtheriae* (causative agent of diphtheria); *Cryptosporidium parvum; Shigella dysenteriae* and *Escherichia coli* (causative agents of dysentery); *Burkholderia mallei* (causative agent of glanders); *Listeria monocytogenes* (causative agent of listerosis); *Burkholderia pseudomallei* (causative agent of meliodosis); *Yersinia pestis* (causative agent of plague); *Francisella tularensis* (causative agent of tularemia); *Chlamydia psittaci* (causative agent of psittacosis); *Coxiella burtetii* (causative agent of Q fever); *Ricketsia rickettsii* (causative agent of Rocky Mountain spotted fever); *Rickettsia prowazekii* and *Rickettsia typhi* (causative agents of typhus); *Coccidioides immitis* (causative agent of coccidiomycosis); Eastern, Western, and Venezuelan equine encephalitis viruses (causative agents of Equine encephalitis); Japanese encephalitis virus (causative agent of Japanese encephalitis); Rift Valley Fever virus (causative agent of Rift Valley fever); Variola virus (causative agent of smallpox); Yellow fever virus (causative agent of yellow fever); arenavirus (causative agent of Lassa fever and the Argentine, Bolivian, Brazilian, and Venezuelan hemorrhagic fevers); other viruses causative of hemorrhagic fevers; other viruses causative of viral encephalitis; Marburg virus; Ebola virus; Nipad virus; hantavirus; SARS; H1N1 influenza virus.

Furthermore, biological toxins with potential to be used as biological agents include, but are not limited to, ricin (derived from the castor bean *Ricinus communis*); saxitoxin (derived from a dinoflaggelate); staphylococcal entertoxin B (derived from *Staphylococcus aureus*); tetrodotoxin (derived from marine bacteria such as *Vibrio* species and *Pseudoalteromonas tetraodonis*); trichothecene mycotoxins (derived from fungi such as *Fusarium, Trichoderma*, and *Stachybotrys*); botulinum toxin (derived from *Clostridium botulinum*); epsilon toxin (derived from *Clostridium perfringens*); abrin toxin (derived from *Abrus precatorius*).

Along with smallpox, anthrax, plague, botulism, and tularemia, hemorrhagic fever viruses are among the six agents identified by the Centers for Disease Control and Prevention (CDC) as the most likely to be used as biological weapons. Hemorrhagic fever viruses include, but are not limited to, the arenaviridae (e.g., Lujo virus); the bunyaviridae (e.g., hantavirus); nairovirus (e.g., the Crimean-Congo hemorrhagic fever virus); Phlebovirus genus (Rift Valley fever virus); filoviridae (e.g., Ebola and Marburg viruses); and flaviviridae (e.g., dengue, yellow fever, Omsk hemorrhagic fever virus, and Kyasanur Forest disease virus).

While the technology finds use in detecting these and other agents in the context of bioterrorism, the technology is also used to detect the same and/or other agents in other contexts and applications. For example, the technology is useful to analyze samples from diseased patients or other subjects suspected of having a disease or having been exposed to a disease.

5. Reading Apparatus

Embodiments of the technology provided herein comprise a reading apparatus that is configured to accept an assay cartridge (and, accordingly, the technology provides a cartridge configured to be inserted into and interface with the reading apparatus). The reading apparatus is configured to send and receive signals to and from the cartridge. For example, these signals control the assays performed by the cartridge (by the electrochemical analyte sensors) and process assay data that results from said assays. In some embodiments the reading apparatus comprises a demultiplexer for decoding a signal sent by the cartridge. Such a demultiplexer can be provided by software, firmware, by a dedicated integrated circuit, or a combination thereof. Software and firmware updates for providing demultiplexer capabilities can be performed on reading apparatuses currently being used by the installed user base.

Some embodiments of the technology provided herein further comprise functionalities for collecting, storing, and/or analyzing data. For example, in some embodiments the reading apparatus comprises a processor, a memory, and/or a database for, e.g., storing and executing instructions, analyzing data, performing calculations using the data, transforming the data, and storing the data. In some embodiments, the reading apparatus is configured to calculate a function of data received from the cartridge (e.g., from one or more electrochemical analyte sensors). In some embodiments the reading apparatus comprises software configured for medical or clinical results reporting and in some embodiments the apparatus comprises software to support non-clinical results reporting.

Many molecular tests involve determining the presence or absence, or measuring the amount or concentrations of, multiple analytes, and an equation comprising variables representing the properties of multiple analytes produces a value that finds use in making a diagnosis or assessing the presence or qualities of an analyte. As such, in some embodiments the reading apparatus calculates this value and, in some embodiments, presents the value to the user of the device, uses the value to produce an indicator related to the result (e.g., an LED, an icon on an LCD, a sound, or the like), stores the value, transmits the value, or uses the value for additional calculations.

Moreover, in some embodiments a processor is configured to control the reading apparatus. In some embodiments, the processor is used to initiate and/or terminate the measurement and data collection. In some embodiments, the device comprises a user interface (e.g., a keyboard, buttons, dials, switches, and the like) for receiving user input that is used by the processor to direct a measurement. In some embodiments, the device further comprises a data output for transmitting (e.g., by a wired or wireless connection) data to an external destination, e.g., a computer, a display, a network, and/or an external storage medium. Some embodiments provide that the device is a small, handheld, portable device incorporating these features and components. Examples of a reading apparatus are provided in U.S. Pat. Nos. 5,096,669 and 5,821,399, which are both hereby incorporated by reference in their respective entireties for all purposes.

Examples 1. 48-Channel Multiplexed Analyte Assay Cartridge

During the development of embodiments of the technology provided herein, a 48-channel multiplexed analyte assay cartridge was developed and tested. See, e.g., FIG. 3. The cartridge comprises a printed circuit board (PCB) comprising the detection circuits (e.g., 48 analyte detection electrodes, a reference electrode, and a counter electrode). The PCB comprising the detection circuits is produced using thick film processing; however, in some embodiments, the PCB comprising the detection circuits is produced with no thick film processing.

Cross-talk, e.g., between sensors and current carrying elements, is minimized or eliminated by creating an extensive guard shield around all sensitive lines. This reduces the chance of stray currents being measured, e.g., by the amplifiers on the hybrid PCB board. In addition, noise is minimized or eliminated by routing the majority of the analog signals on inner layers sandwiched between ground and power planes. In addition, the guard traces and fills also help to eliminate noise due to the low impedance of its driver.

The reference electrode is a silver/silver chloride (Ag/AgCl) electrode manufactured by screen-printing a silver/silver chloride ink directly onto the PCB. No significant differences were observed between the screen-printed Ag/AgCl electrode and conventional technology, e.g., a chlorodized silver metal electrode on a silicon chip. The counter electrode provides a local current return path for the sensor electrodes. The cartridge comprises 48 sensors arranged in 6 parallel analog circuits (e.g., 6 parallel amperometric channels) each containing 8 working electrodes (e.g., analyte sensors). Each detection electrode is connected to a switch (thus making a total of 48 switches) that places the electrode into an ON or an OFF state. In some embodiments, a switch is used that maximizes performance and minimizes size (e.g., minimizes the footprint required on the PCB). For example, in some embodiment a Vishay/Siliconix DG612AEQ-T1-E3 switch is used for the shift register.

The PCB circuit has an 8-channel shift register whereby each channel controls a set of 6 ON/OFF switches, one in each amperometric channel. The shift register thus switches ON and OFF a set of 6 switches simultaneously, one in each amperometric (analog current) channel. Thus, the 48 switches are controlled by the shift register, which responds to a digital signal (e.g., provided by a microprocessor) to effect ON and OFF switching events for the 48 switches and associated sensors. As an example, by switching at a rate of 2 Hz, 2 measurements are taken per second and thus all 48 electrodes are read in 4 seconds. Accordingly, 5 independent readings at each electrode are collected in 20 seconds.

A hybrid PCB board interfaces with the cartridge PCB by an 18-pin connector. The hybrid PCB board comprises 6 amperometric measurement channels, power regulation, a microprocessor, and an analog-to-digital (A/D) conversion component to read the signals and send data to the apparatus. The hybrid board PCB interfaces with the handheld apparatus through a serial communication interface. While the embodiment described in this example comprises a particular configuration of electrodes, the hybrid PCB board may be readily reconfigured to accommodate different electrode configurations.

As shown in FIG. 3, embodiments of the cartridge comprise a fluid pack, a fluid pump, and a port for sample injection. These components are connected by microfluidic channels that provide samples and reagents to the electrode analyte sensors, which are aligned along the linear fluid path. The cartridge comprises conductivity bars (e.g., Hct bars, e.g., hematocrit bars) along the microfluidic channel, e.g., to detect the presence of fluid during microfluidics operations.

The cartridge comprises a top cover and a base, which, in some embodiments, are made of molded plastic that provide a mechanical structure to support the circuits and fluidic components. Metal, cardboard, paper, rubber, and other materials are used in some embodiments for the top cover and for the base.

In some embodiments, the cartridge is designed to detect a nucleic acid, e.g., a PCR amplicon. According to these embodiments, a DNA capture sequence is chemically bound to 0.2 micron beads. The beads are then spotted onto each sensor as part of the cartridge production process.

2. Testing the 48-Channel Multiplexed Analyte Assay Cartridge

During the development of embodiments of the 48-channel multiplexed analyte assay cartridge, test data were collected.

As one application in which the present technology finds use, tests were performed to detect the presence of a nucleic acid (e.g., an amplified DNA product from a polymerase chain reaction (e.g., an "amplicon")).

These tests comprised the use of a liquid test sample comprising a DNA construct having two portions: one portion is a DNA complementary to the DNA capture sequence attached to the beads and a second portion is a detectable moiety attached to the DNA, e.g., a biotin. A conjugate (e.g., comprising streptavidin linked to an enzyme (e.g., ALP)) was also added to the liquid sample. The streptavidin binds to the biotin and the enzyme cleaves an electrogenic substrate (e.g., also provided in the test sample) to produce an electronegative species that is detected at the electrode.

For this testing, a single type of nucleic acid capture bead was spotted on all 48 sensors and tests were conducted to detect the amplicon with the sensors.

Using a 2 Hz sampling rate (e.g., 50 ms ON and 450 ms OFF), data were collected that showed a steady low-noise signal from each analog channel. In this particular embodiment, each of the 8 sensors in each analog channel was normally ON and the 8 signals were summed on each monitored analog channel. Then, the signals at each of the individual sensors were measured by switching OFF one switching channel (e.g., comprising 6 switches, one each in the 6 analog circuit channels) of the 8-channel shift register and measuring the change in the analog signals relative to the total signal when all 8 switches are ON. The change in current was attributable to the current level for the sensor(s) switched OFF. In other embodiments, each of the 8 sensors in each analog channel was normally OFF and the signals at each of the individual sensors were measured by switching ON one switching channel (comprising 6 switches, one each in the 6 analog circuit channels) of the 8-channel shift register and measuring the change in the analog signals relative to the zeroed signal when all 8 switches are OFF. The change in current was attributable to the current level for the sensor(s) switched ON. In additional testing, these two modes of data acquisition (e.g., one sensor/channel ON or one sensor/channel OFF) were compared and both approaches yielded similar results.

During a test of an embodiment of a 48-sensor multiplexed array as described herein, data collected (e.g., the mean value of 10 measurements taken for each sensor) demonstrated that similar signals were obtained for all 48 sensors. These data indicate consistent coverage of the sensors with the beads, consistent sample loading, and the acquisition of 48 signals from the 6×8 multiplexed sensor array.

During testing of an embodiment of the technology, data collected for a 50 ms switching event demonstrated that the signal quickly equilibrates after the switching event. The signal during the switching events was consistent, regular, and predictable. This allows the signal to be read before equilibration is complete by applying a correction factor. For example, in some embodiments, a mathematical model of the signal response to the OFF and ON switching events provides for an increased switching frequency (e.g., an interval less than 50 ms). Accordingly, in some embodiments, a sampling rate faster than 2 Hz is used to acquire more data per unit of time.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in pharmacology, biochemistry, medical science, or related fields are intended to be within the scope of the following claims.

We claim:

1. A method for detecting one or more analytes in a sample, comprising:
    a) providing a cartridge for sensing an analyte in a sample, said cartridge comprising:
        1) 48 analyte sensors for assaying the sample;
        2) 6 measurement channels electrically coupled to said 48 analyte sensors;
        3) an 8-channel shift register electrically coupled to said 48 analyte sensors;
        4) a multiplexer electronically connected to said 48 analyte sensors configured to receive a data signal and output an output signal;
        5) a data output electronically connected to said multiplexer; and
    b) exposing said cartridge to said sample and detecting one or more analytes in said sample.

2. The method of claim 1, wherein at least one of said analyte sensors is an electrochemical analyte sensor or a light sensor that detects light and outputs an electrical signal.

3. The method of claim 1, further comprising an interface for connecting said cartridge to a reading apparatus, wherein said interface transmits signals between said cartridge and said reading apparatus.

4. The method of claim 3, wherein said cartridge further comprises:
    7) a first interface component configured to mate with said reading apparatus and communicate with said reading apparatus; and wherein said reading apparatus comprises:
        i) a second interface component configured to mate with said cartridge and communicate with said cartridge; and
        ii) a microprocessor configured to decode said output signal.

5. The method of claim 1 wherein an output signal from said data output comprises a sampled portion of a data signal from at least one of said analyte sensors.

6. The method of claim 1, wherein a data signal is sampled during a timeslot for 0.01-10 seconds.

7. The method of claim 1, wherein said cartridge is configured to acquire 2 measurements per second.

8. The method of claim 1, wherein said cartridge further comprises a screen-printed silver/silver chloride electrode.

9. The method of claim 1, wherein a printed circuit board comprises said 48 analyte sensors.

10. The method of claim 1, wherein said analyte is selected from the group consisting of: a nucleic acid, an antigen, an enzyme, a protein, a toxin, a biochemical metabolite, a biological ion, and a respiratory gas.

11. The method of claim 1, wherein said analyte sensors produce a signal that is, or is a combination of, a type selected from the group consisting of: amperometric, conductimetric, and potentiometric.

12. The method of claim 1, wherein at least one sensor of said 48 analyte sensors comprises a nucleic acid capture element.

13. The method of claim 1, wherein at least one sensor of said 48 analyte sensors detects an electrogenic species derived from an enzyme reaction associated with nucleotide capture.

14. The method of claim 1, wherein said shift register controls the ON/OFF state of each analyte sensor of said 48 analyte sensors.

15. The method of claim 1, wherein said shift register simultaneously controls the ON/OFF state of 6 analyte sensors.

16. The method of claim 1, wherein said shift register simultaneously controls the ON/OFF state of 6 analyte sensors, one in each measurement channel.

17. The method of claim 16, wherein said measurement channel carries the multiplexed signals from 8 analyte sensors.

* * * * *